(12) United States Patent
Knudsen et al.

(10) Patent No.: US 7,481,807 B2
(45) Date of Patent: Jan. 27, 2009

(54) RADIOFREQUENCY ARTHROSCOPIC ABLATION DEVICE

(75) Inventors: Katherine A. Knudsen, San Jose, CA (US); Duane W. Marion, Santa Clara, CA (US); Hugh R. Sharkey, Redwood City, CA (US)

(73) Assignee: Oratec Interventions, Inc., Menlo Park, CA (US)

( * ) Notice: Subject to any disclaimer, the term of this patent is extended or adjusted under 35 U.S.C. 154(b) by 363 days.

(21) Appl. No.: 10/490,979

(22) PCT Filed: Feb. 12, 2003

(86) PCT No.: PCT/US03/04139

§ 371 (c)(1),
(2), (4) Date: Sep. 1, 2004

(87) PCT Pub. No.: WO03/068095

PCT Pub. Date: Aug. 21, 2003

(65) Prior Publication Data

US 2005/0027235 A1    Feb. 3, 2005

Related U.S. Application Data

(60) Provisional application No. 60/356,612, filed on Feb. 12, 2002.

(51) Int. Cl.
*A61B 18/18*    (2006.01)
(52) U.S. Cl. .............. 606/41; 606/45; 606/49; 606/50
(58) Field of Classification Search ............. 606/27–52
See application file for complete search history.

(56) References Cited

U.S. PATENT DOCUMENTS

| 3,920,021 A | 11/1975 | Hiltebrandt |
| 3,970,088 A | 7/1976 | Morrison |
| 3,987,795 A | 10/1976 | Morrison |

(Continued)

FOREIGN PATENT DOCUMENTS

WO    WO 90/07303    7/1990

(Continued)

OTHER PUBLICATIONS

"ElectroSurgical Probe, Ligament Chisel™ and Micro Ligament Chisel™,"Oratec™, 2 pages.

(Continued)

*Primary Examiner*—Roy D Gibson
(74) *Attorney, Agent, or Firm*—Fish & Richardson P.C.

(57) ABSTRACT

A surgical device includes an elongated shaft having first and second electrically isolated electrodes coupled to the shaft such that an exposed portion of the second electrode is disposed around only part of a circumference of the elongated shaft, and includes a portion that is spaced proximally from the first electrode. Another surgical device also includes an elongated shaft having first and second electrically isolated electrodes coupled to the shaft, wherein the shaft includes a first side, and exposed surfaces of the first and second electrodes are side-facing toward the first side. Various embodiments of a "cool back" are provided, allowing arthroscopic surgery on a first side of a device without tissue effects on a back side of the device.

49 Claims, 11 Drawing Sheets

U.S. PATENT DOCUMENTS

| | | |
|---|---|---|
| 4,043,342 A | 8/1977 | Morrison |
| 4,074,718 A | 2/1978 | Morrison |
| 4,116,198 A | 9/1978 | Roos |
| 4,202,337 A | 5/1980 | Clarke et al. |
| 4,476,862 A | 10/1984 | Pao |
| 4,483,338 A | 11/1984 | Bloom et al. |
| 4,532,924 A | 8/1985 | Auth et al. |
| 4,548,207 A | 10/1985 | Reimels |
| 4,593,691 A | 6/1986 | Lindstrom et al. |
| 4,674,499 A | 6/1987 | Pao |
| 4,765,331 A | 8/1988 | Petruzzi et al. |
| 4,805,616 A | 2/1989 | Pao |
| 4,823,791 A | 4/1989 | D'Amelio et al. |
| 4,832,048 A | 5/1989 | Cohen |
| 4,936,281 A | 6/1990 | Stasz |
| 4,966,597 A | 10/1990 | Cosman |
| 4,976,711 A | 12/1990 | Parins et al. |
| 4,998,933 A | 3/1991 | Eggers et al. |
| 5,009,656 A | 4/1991 | Reimels |
| 5,019,076 A | 5/1991 | Yamanashi et al. |
| 5,035,696 A | 7/1991 | Rydell |
| 5,080,660 A | 1/1992 | Buelina |
| 5,085,659 A | 2/1992 | Rydell |
| 5,089,002 A | 2/1992 | Kirwan, Jr. |
| 5,098,431 A | 3/1992 | Rydell |
| 5,122,138 A | 6/1992 | Manwaring |
| 5,178,620 A | 1/1993 | Eggers et al. |
| 5,192,280 A | 3/1993 | Parins |
| 5,197,963 A | 3/1993 | Parins |
| 5,217,458 A | 6/1993 | Parins |
| 5,273,524 A | 12/1993 | Fox et al. |
| 5,277,696 A | 1/1994 | Hagen |
| 5,348,554 A | 9/1994 | Imran et al. |
| 5,366,443 A | 11/1994 | Eggers |
| 5,383,876 A | 1/1995 | Nardella |
| 5,419,767 A | 5/1995 | Eggers et al. |
| 5,451,223 A | 9/1995 | Ben-Shimon |
| 5,454,809 A | 10/1995 | Janssen |
| 5,458,596 A | 10/1995 | Lax et al. |
| 5,486,161 A | 1/1996 | Lax et al. |
| RE35,187 E | 3/1996 | Gortz |
| 5,500,012 A | 3/1996 | Brucker et al. |
| 5,514,130 A | 5/1996 | Baker |
| 5,529,214 A | 6/1996 | Lasonde et al. |
| 5,545,161 A | 8/1996 | Imran |
| 5,549,605 A | 8/1996 | Hahnen |
| 5,556,397 A | 9/1996 | Long et al. |
| 5,569,242 A | 10/1996 | Lax et al. |
| 5,573,533 A | 11/1996 | Strul |
| 5,582,610 A | 12/1996 | Grossi et al. |
| 5,599,346 A | 2/1997 | Edwards et al. |
| 5,599,349 A | 2/1997 | D'Amelio |
| 5,626,576 A | 5/1997 | Janssen |
| 5,643,197 A | 7/1997 | Brucker et al. |
| 5,658,278 A | 8/1997 | Imran et al. |
| 5,681,282 A | 10/1997 | Eggers et al. |
| 5,683,366 A | 11/1997 | Eggers et al. |
| 5,697,281 A | 12/1997 | Eggers et al. |
| 5,697,356 A | 12/1997 | Chappell |
| 5,697,882 A | 12/1997 | Eggers et al. |
| 5,697,909 A | 12/1997 | Eggers et al. |
| 5,697,925 A | 12/1997 | Taylor |
| 5,700,262 A | 12/1997 | Acosta et al. |
| 5,730,742 A | 3/1998 | Wojciechowicz |
| 5,743,870 A | 4/1998 | Edwards |
| 5,762,626 A | 6/1998 | Lundquist et al. |
| 5,766,153 A | 6/1998 | Eggers et al. |
| 5,785,705 A | 7/1998 | Baker |
| 5,800,431 A | 9/1998 | Brown |
| 5,810,764 A | 9/1998 | Eggers et al. |
| 5,814,043 A | 9/1998 | Shapeton |
| 5,823,994 A | 10/1998 | Sharkey et al. |
| 5,843,019 A | 12/1998 | Eggers et al. |
| 5,860,974 A | 1/1999 | Abele |
| 5,871,469 A | 2/1999 | Eggers et al. |
| 5,873,855 A | 2/1999 | Eggers et al. |
| 5,888,198 A | 3/1999 | Eggers et al. |
| 5,891,095 A | 4/1999 | Eggers et al. |
| 5,902,272 A | 5/1999 | Eggers et al. |
| 5,919,188 A | 7/1999 | Shearon et al. |
| 5,925,045 A | 7/1999 | Reimels et al. |
| 5,944,715 A | 8/1999 | Goble et al. |
| 5,954,716 A | 9/1999 | Sharkey et al. |
| 5,976,127 A | 11/1999 | Lax |
| 5,980,504 A | 11/1999 | Sharkey et al. |
| 5,991,650 A | 11/1999 | Swanson et al. |
| 6,004,319 A | 12/1999 | Goble et al. |
| 6,004,320 A | 12/1999 | Casscells et al. |
| 6,007,533 A | 12/1999 | Casscells et al. |
| 6,007,570 A | 12/1999 | Sharkey et al. |
| 6,024,733 A | 2/2000 | Eggers et al. |
| 6,032,674 A | 3/2000 | Eggers et al. |
| 6,045,532 A | 4/2000 | Eggers et al. |
| 6,047,700 A | 4/2000 | Eggers et al. |
| 6,053,172 A | 4/2000 | Hovda et al. |
| 6,063,079 A | 5/2000 | Hovda et al. |
| 6,066,134 A | 5/2000 | Eggers et al. |
| 6,068,628 A | 5/2000 | Fanton et al. |
| 6,073,051 A | 6/2000 | Sharkey et al. |
| 6,086,585 A | 7/2000 | Hovda et al. |
| 6,090,106 A | 7/2000 | Goble et al. |
| 6,095,149 A | 8/2000 | Sharkey et al. |
| 6,099,514 A | 8/2000 | Sharkey et al. |
| 6,102,046 A | 8/2000 | Weinstein et al. |
| 6,105,581 A | 8/2000 | Eggers et al. |
| 6,106,522 A * | 8/2000 | Fleischman et al. ........... 606/41 |
| 6,109,268 A | 8/2000 | Thapliyal et al. |
| 6,113,597 A | 9/2000 | Eggers et al. |
| 6,117,109 A | 9/2000 | Eggers et al. |
| 6,122,549 A | 9/2000 | Sharkey et al. |
| 6,126,682 A | 10/2000 | Sharkey et al. |
| 6,135,999 A | 10/2000 | Fanton et al. |
| 6,142,992 A | 11/2000 | Cheng et al. |
| 6,149,620 A | 11/2000 | Baker et al. |
| 6,159,194 A | 12/2000 | Eggers et al. |
| 6,159,208 A | 12/2000 | Hovda et al. |
| 6,162,217 A | 12/2000 | Kannenberg et al. |
| 6,168,593 B1 | 1/2001 | Sharkey et al. |
| 6,176,857 B1 | 1/2001 | Ashley |
| 6,179,824 B1 | 1/2001 | Eggers et al. |
| 6,179,836 B1 | 1/2001 | Eggers et al. |
| 6,183,469 B1 | 2/2001 | Thapliyal et al. |
| 6,190,381 B1 | 2/2001 | Olsen et al. |
| 6,203,542 B1 | 3/2001 | Ellsberry et al. |
| 6,210,402 B1 | 4/2001 | Olsen et al. |
| 6,214,001 B1 | 4/2001 | Casscells et al. |
| 6,224,592 B1 | 5/2001 | Eggers et al. |
| 6,228,078 B1 | 5/2001 | Eggers et al. |
| 6,235,020 B1 | 5/2001 | Cheng et al. |
| 6,238,391 B1 | 5/2001 | Olsen et al. |
| 6,246,913 B1 | 6/2001 | Sharkey |
| 6,254,600 B1 | 7/2001 | Willink |
| 6,258,086 B1 | 7/2001 | Ashley et al. |
| 6,261,311 B1 | 7/2001 | Sharkey et al. |
| 6,264,650 B1 | 7/2001 | Hovda et al. |
| 6,264,651 B1 | 7/2001 | Underwood et al. |
| 6,264,652 B1 | 7/2001 | Eggers et al. |
| 6,269,636 B1 | 8/2001 | Hatzilakos |
| 6,277,112 B1 | 8/2001 | Underwood et al. |
| 6,277,319 B2 | 8/2001 | Hardgrove et al. |
| 6,283,960 B1 | 9/2001 | Ashley |
| 6,283,961 B1 | 9/2001 | Underwood et al. |
| 6,290,715 B1 | 9/2001 | Sharkey et al. |
| 6,296,638 B1 * | 10/2001 | Davison et al. ............... 606/41 |

| | | |
|---|---|---|
| 6,296,683 B1 | 10/2001 | Koch |
| 6,309,387 B1 | 10/2001 | Eggers et al. |
| 6,312,408 B1 | 11/2001 | Eggers et al. |
| 6,322,549 B1 | 11/2001 | Eggers et al. |
| 6,350,262 B1 | 2/2002 | Ashley |
| 6,355,032 B1 | 3/2002 | Hovda et al. |
| 6,358,273 B1 | 3/2002 | Strul et al. |
| 6,363,937 B1 | 4/2002 | Hovda et al. |
| 6,379,350 B1 * | 4/2002 | Sharkey et al. ............. 606/41 |
| 6,379,351 B1 | 4/2002 | Thapliyal et al. |
| 6,391,025 B1 | 5/2002 | Weinstein et al. |
| 6,391,028 B1 | 5/2002 | Fanton et al. |
| 6,416,507 B1 | 7/2002 | Eggers et al. |
| 6,416,508 B1 | 7/2002 | Eggers et al. |
| 6,432,103 B1 | 8/2002 | Ellsberry et al. |
| 6,432,105 B1 | 8/2002 | Ellman et al. |
| 6,440,141 B1 | 8/2002 | Philippon |
| 6,461,350 B1 | 10/2002 | Underwood et al. |
| 6,461,353 B1 | 10/2002 | Baker, Jr. et al. |
| 6,461,354 B1 | 10/2002 | Olsen et al. |
| 6,461,357 B1 | 10/2002 | Sharkey et al. |
| 6,464,695 B2 | 10/2002 | Hovda et al. |
| 6,468,270 B1 | 10/2002 | Hovda et al. |
| 6,468,274 B1 | 10/2002 | Alleyne et al. |
| 6,482,201 B1 | 11/2002 | Olsen et al. |
| 6,482,204 B1 | 11/2002 | Lax et al. |
| 6,517,568 B1 | 2/2003 | Sharkey et al. |
| 6,540,741 B1 | 4/2003 | Underwood et al. |
| 6,544,260 B1 | 4/2003 | Markel et al. |
| 6,544,261 B2 | 4/2003 | Ellsberry et al. |
| 6,547,810 B1 | 4/2003 | Sharkey et al. |
| 6,551,279 B1 | 4/2003 | Hyum |
| 6,557,559 B1 | 5/2003 | Eggers et al. |
| 6,575,968 B1 | 6/2003 | Eggers et al. |
| 6,582,423 B1 | 6/2003 | Thapliyal et al. |
| 6,589,237 B2 | 7/2003 | Wolszko et al. |
| 6,595,990 B1 | 7/2003 | Weinstein et al. |
| 6,602,248 B1 | 8/2003 | Sharps et al. |
| 6,620,155 B2 | 9/2003 | Underwood et al. |
| 6,623,454 B1 | 9/2003 | Eggers et al. |
| 6,632,193 B1 | 10/2003 | Davison et al. |
| 6,632,220 B1 | 10/2003 | Eggers et al. |
| 6,638,276 B2 | 10/2003 | Sharkey et al. |
| 6,645,203 B2 | 11/2003 | Sharkey et al. |
| 6,695,839 B2 | 2/2004 | Sharkey et al. |
| 6,699,244 B2 | 3/2004 | Carranza et al. |
| 6,726,685 B2 | 4/2004 | To et al. |
| 6,733,496 B2 | 5/2004 | Sharkey et al. |
| 6,749,605 B2 | 6/2004 | Ashley et al. |
| 6,757,565 B2 | 6/2004 | Sharkey et al. |
| 2001/0001314 A1 | 5/2001 | Davison et al. |
| 2001/0020107 A1 | 9/2001 | Walter et al. |
| 2001/0025176 A1 | 9/2001 | Ellsberry et al. |
| 2001/0029370 A1 | 10/2001 | Hovda et al. |
| 2001/0029373 A1 | 10/2001 | Baker et al. |
| 2001/0031963 A1 | 10/2001 | Sharkey et al. |
| 2001/0051802 A1 | 12/2001 | Woloszko et al. |
| 2002/0022830 A1 | 2/2002 | Sharkey et al. |
| 2002/0026186 A1 | 2/2002 | Woloszko et al. |
| 2002/0068930 A1 | 6/2002 | Tasto et al. |
| 2002/0095151 A1 | 7/2002 | Dahla et al. |
| 2002/0095152 A1 | 7/2002 | Ciarrocca et al. |
| 2002/0099366 A1 | 7/2002 | Dahla et al. |
| 2002/0120259 A1 | 8/2002 | Lettice et al. |
| 2002/0128641 A1 | 9/2002 | Underwood et al. |
| 2002/0133149 A1 | 9/2002 | Bessette |
| 2002/0188290 A1 | 12/2002 | Sharkey et al. |
| 2002/0193789 A1 | 12/2002 | Underwood et al. |
| 2003/0009164 A1 | 1/2003 | Woloszko et al. |
| 2003/0014051 A1 | 1/2003 | Woloszko |
| 2003/0028189 A1 | 2/2003 | Woloszko et al. |
| 2003/0040742 A1 | 2/2003 | Underwood et al. |
| 2003/0055418 A1 | 3/2003 | Tasto et al. |
| 2003/0084907 A1 | 5/2003 | Pacek et al. |
| 2003/0088245 A1 | 5/2003 | Woloszko et al. |
| 2003/0097129 A1 | 5/2003 | Davison et al. |
| 2003/0120269 A1 | 6/2003 | Bessette et al. |
| 2003/0130655 A1 | 7/2003 | Woloszko et al. |
| 2003/0130738 A1 | 7/2003 | Hovda et al. |
| 2003/0139789 A1 | 7/2003 | Trinnereim et al. |
| 2003/0158545 A1 | 8/2003 | Hovda et al. |
| 2003/0163178 A1 | 8/2003 | Davison et al. |
| 2003/0171743 A1 | 9/2003 | Tasto et al. |

FOREIGN PATENT DOCUMENTS

| | | |
|---|---|---|
| WO | WO 92/21278 | 12/1992 |
| WO | WO 94/26228 | 11/1994 |
| WO | WO 95/13027 | 5/1995 |
| WO | WO 97/48346 | 12/1997 |
| WO | WO 98/07468 | 2/1998 |
| WO | WO 98/11944 | 3/1998 |
| WO | WO 98/34549 | 8/1998 |
| WO | WO 98/34558 | 8/1998 |
| WO | WO 99/47058 | 9/1999 |
| WO | WO 99/48430 | 9/1999 |
| WO | WO 99/48430 A | 9/1999 |
| WO | WO 01/52759 | 7/2001 |
| WO | WO 02/098309 | 12/2002 |
| WO | WO 03/037195 | 5/2003 |
| WO | WO 03/065917 | 8/2003 |
| WO | WO 03/068095 | 8/2003 |

OTHER PUBLICATIONS

"Vulcan™ Saphyre™ Bipolar Ablation Probes," Oratec™, 1 page.
"Vulcan™ ElectroSurgical Probes—Vulcan™ Albator™—S Probes," Oratec, 1 page.
"Ligament Chisel™ ElectroSurgical Cutting Probes," Thermal Science and Technology from Oratec®, Oratec Interventions, Inc., 2001, 2 pages.
"Vulcan® EAS® 2mm Ablator—Ablation Probe," Thermal Science and Technology from Oratec®, Oratec Interventions, Inc., 2000, 2 pages.
"Vulcan® EAS® 2mm Ablator™-S 90°—Suction Ablation Probe," Thermal Science and Technology from Oratec®, Oratec Interventions, Inc. 2000, 2 pages.
"Vulcan™ EAS™ Ablator™—ElectroThermal Arthroscopy™ Probes," Oratec®, Oratec Interventions, Inc., 1999, 1 page.
"MiniTAC™ and MicroTAC-S™—ElectroThermal Arthroscopy Probes, Tissue Temperature Control in Areas of Restricted Access—Micro Ligament Chisel™ Probes," Oratec®, Oratec Interventions, Inc., 1999, 2 pages.
"MiniTAC™ and MicroTAC-S™—ElectroThermal Arthroscopy Probes, Tissue Temperature Control in Areas of Restricted Access—Micro Ligament Chisel™ Probes," Oratec®, Oratec Interventions, Inc., 2000, 2 pages.
"Ligament Chisel™—ElectroSurgical Cutting Probes," Oratec®, Oratec Interventions, Inc., 2000, 2 pages.
"Vulcan™ EAS™ Ablator™—ElectroThermal Arthroscopy™ Probes," Oratec®, Oratec Interventions, Inc., 2000, 1 page.
"TAC™ C II—Tissue Temperature Control ElectroThermal Anthroscopy Probe," Thermal Science and Technology from Oratec®, Oratec Interventions, Inc., 2000, 2 pages.
"ORAflex™—ElectroThermal Probe," Oratec®, Oratec Interventions, Inc., 1999, 1 page.
"Vulcan® EAS™ 2mm Ablator™—Ablation Probe," Oratec®, Oratec Interventions, Inc., 2000, 2 pages.
"Temperature Matters," Oratec®, Oratec Interventions, Inc., 1998, 2 pages.
"Temperature Control (TAC™)—ElectroThermal Arthroscopy™ Probes," Oratec®, Oratec Interventions, Inc., 1998, 2 pages.
"MiniTAC™ and MicroTAC-S™—ElectroThermal Arthroscopy Probes, Tissue Temperature Control in Areas of Restricted Access—Micro Ligament Chisel™ Probes," Oratec®, Oratec Interventions, Inc., 1999, 2 pages.

"Ligament Chisel™—ElectroSurgical Cutting Probes," Oratec®, Oratec Interventions, Inc., 1998, 2 pages.

"Temperature Matters," Oratec®, Oratec Interventions, Inc., 1998, 2 pages.

"Ligament Chisel™—ElectroSurgical Cutting Probes," Oratec®, Oratec Interventions, Inc., 1998, 2 pages.

"Temperature Control (TAC™)—ElectroThermal Arthroscopy™ Probes," Oratec®, Oratec Interventions, Inc., 1999, 2 pages.

"An Amazing Machine—Oratec © Vulcan™ EAS™ ElectroThermal Arthroscopy System,"Oratec®, Oratec Interventions, Inc., 1999, 6 pages.

"Vulcan® EAS® Ablator™-S 90°—Suction Ablation Probe," Thermal Science and Technology fromf Oratec®, Oratec Interventions, Inc., 2000, 2 pages.

"Micro Ablator™ and Micro Ligament Chisel™—Small Joint ElectroThermal Ablation Probes," Oratec®, Oratec Interventions, Inc., 2002, 2 pages.

"Ligament Chisel™—ElectroSurgical Cutting Probes," Oratec®, Oratec Interventions, Inc., 2001, 2 pages.

"Vulcan® EAS® Ablator™-S 2mm—Suction Ablation Probe," Thermal Science and Technology from Oratec®, Oratec Interventions, Inc., 2002, 2 pages.

"Eflex™—ElectroThermal Probes for Hip Arthroscopy," Thermal Science and Technology from Oratec®, Oratec Interventions, Inc., 2002, 2 pages.

"Vulcan® EAS® 2mm Ablator—Ablation Probe," Thermal Science and Technology from Oratec®, Oratec Interventions, Inc., 2000, 2 pages.

"TAC™-C II—Tissue Temperature Control ElectroThermal Anthroscopy Probe," Thermal Science and Technology from Oratec®, Oratec Interventions, Inc., 2000, 2 pages.

"Tissue Temperature Control," Thermal Science and Technology from Oratec®, Oratec Interventions, Inc., 2001, 8 pages.

"Vulcan™ TAC™ Monopolar ElectroThermal Probes," History, Oratec®, Oratec Interventions, Inc., 2 pages.

"Vulcan™ ElectroSurgical Probes—Vulcan Ligament Chisel™ Vulcan™ Micro Ligament Chisel™," History, Oratec®, Oratec Interventions, Inc., 2 pages.

"Vulcan™ ElectroSurgical Probes—Vulcan™ Ablator™ Probes," History, Oratec®, Oratec Interventions, Inc., 2 pages.

"Vulcan™ Eflex™ Probes," History, Oratec®, Oratec Interventions, Inc., 2 pages.

"Vulcan® ElectroThermal™ Probes—Vulcan® TAC-S™ Vulcan® TAC-S™, Angled Vulcan® TAC-C™, TAC-C™ II Vulcan® MiniTAC-S™ Vulcan® MicroTAC-S™ Vulcan® MicroTAC-S™, Angled," History, Oratec®, Oratec Interventions, Inc., 1999, 2 pages.

"Vulcan™ ElectroSurgical Probes—Vulcan™ Ligament Chisel™—Vulcan™ Micro Ligament Chisel™," History, Oratec®, Oratec Interventions, Inc., 1999, 3 pages.

"Vulcan™ EAS™ ElectroThermal Arthroscopy System," Oratec®, Oratec Interventions, Inc., 2 pages.

"Vulcan™ EAS™ System Description," Oratec®, Oratec Interventions, Inc., 15 pages.

Communication from the European Patent Office, Application No. 03 710 983.2, Mar. 14, 2006, (4 pages).

* cited by examiner

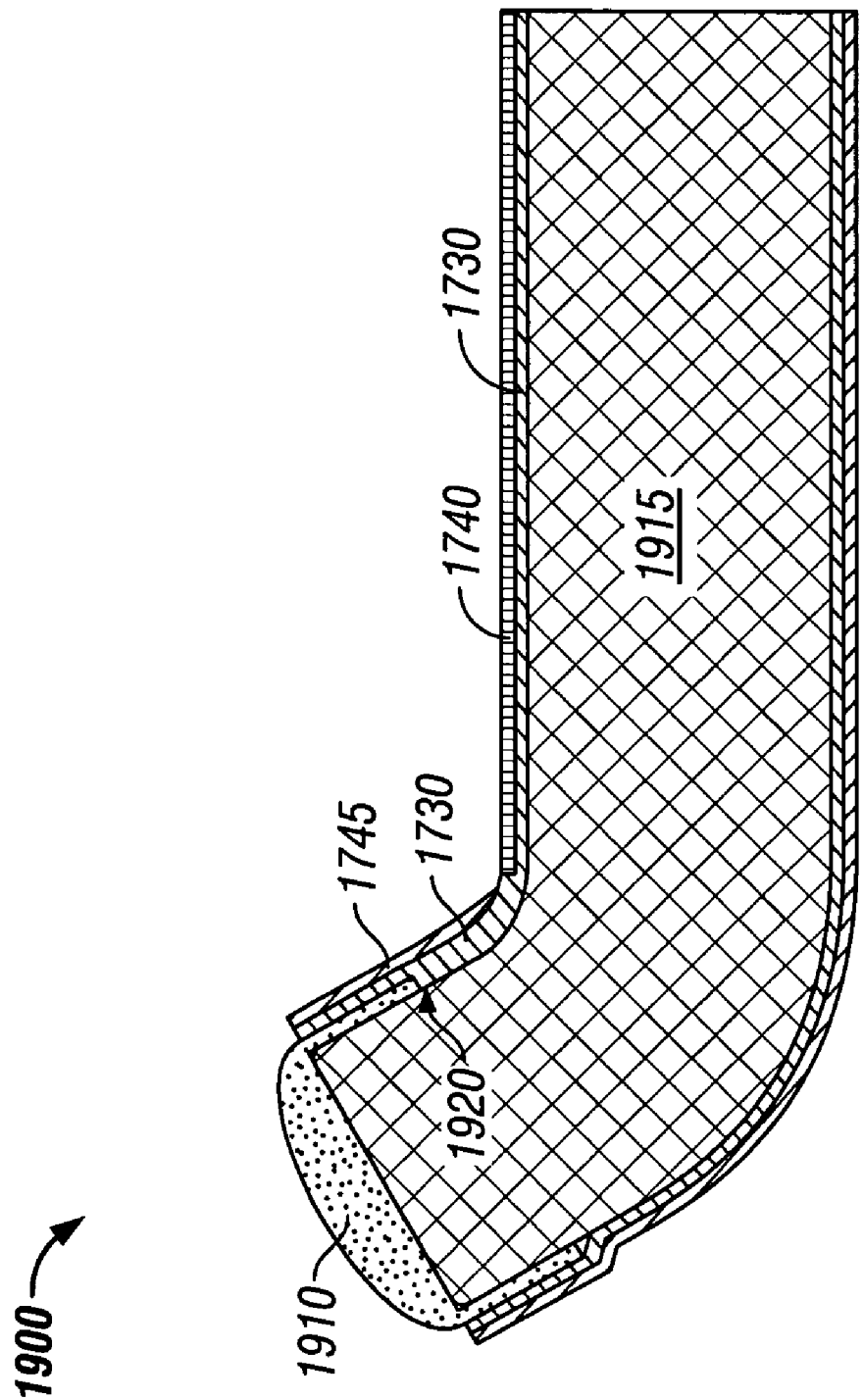

RADIOFREQUENCY ARTHROSCOPIC ABLATION DEVICE

CROSS-REFERENCE TO RELATED APPLICATION

The present application is a National Stage of International Application No. PCT/US03/04139, filed Feb. 12, 2003, which claims priority from U.S. patent application Ser. No. 60/356,612, filed Feb. 12, 2002, and titled "Arthroscopic Ablation Device," the entire contents of which are incorporated herein by reference.

TECHNICAL FIELD

Implementations relate to surgical devices and methods for applying thermal and/or electrical energy to organic material such as biological tissue to modify the characteristics of the tissue for therapeutic purposes. More particularly, disclosed implementations are directed to electrosurgical devices utilizing radio frequency ("RF") energy to cut, coagulate, and/or ablate tissue during a medical procedure for treatment and therapy.

BACKGROUND

Traditional open surgery is performed to repair various joints and orthopedic problems throughout the human body. Open surgery often has long recovery times with large scars and requires intensive rehabilitation. There is a large cost associated with performing these procedures, including operating room time, personnel needed, and use of medical materials.

Arthroscopic surgery is becoming increasingly popular, compared to traditional open surgery, because arthroscopic surgery generally does less damage, is less invasive, is safer, and produces less scarring in and around joints. Further, compared to traditional open surgery, arthroscopic surgery results in faster healing and a quicker return of a patient to full productivity, and reduces costs.

SUMMARY

An apparatus and method are disclosed, for example, to selectively cut and ablate body tissue during a medical procedure such as arthroscopic surgery. The apparatus and method are configured and used for effective cutting and ablation of target tissue while giving the surgeon a precise and controlled surface for scraping tissue from bone or removing tissue within the surgical field for appropriate treatment and therapy. The apparatus can direct the energy source (for example, RF) to the tissue (for example, a tendon or a ligament) and apply RF to relatively cleanly and smoothly ablate the tissue. The apparatus can target certain tissues to be treated with high temperatures while protecting non-targeted tissues from thermal effect, thereby increasing the viability of tissues and promoting complete recovery. Accordingly, some procedures that have been considered too awkward or difficult to perform effectively by arthroscopy can now be performed more effectively using arthroscopic devices. The apparatus and method are applicable in a wide variety of medical procedures on a wide range of different bodily tissues. The apparatus is also simple and inexpensive to manufacture, and is compatible with conventional systems and procedures.

According to one aspect, a surgical device includes an elongated shaft, a first electrode coupled to the shaft, and a second electrode coupled to the shaft. The second electrode is electrically isolated from the first electrode, includes an exposed portion that is disposed around only part of a circumference of the elongated shaft, and includes a portion that is spaced proximally from the first electrode.

Embodiments of this aspect may include one or more of the following features.

A conductor includes the second electrode, the conductor being disposed around only a portion of the circumference of the elongated shaft. A layer of insulation is disposed over at least a portion of the conductor and includes a window that defines the exposed portion of the second electrode. The layer of insulation is also disposed over at least a designated part of the elongated shaft around which the conductor is not disposed, wherein the designated part provides an insulated area that is configured to shield adjacent tissue during electrosurgery. The layer of insulation provides both thermal and electrical insulation.

The elongated shaft includes a distal portion, and the first electrode is coupled to the distal portion of the elongated shaft and is side-facing. The shaft includes a bend in the distal portion proximal to the first electrode and includes a distal tip, and the side-facing first electrode is disposed at the distal tip. The elongated shaft defines a longitudinal axis and includes a first side extending longitudinally along the axis. The side-facing first electrode faces toward the first side, and the exposed portion of the second electrode includes a portion facing the first side. A conductor includes the second electrode, and the conductor is disposed around only a portion of the circumference of the elongated shaft. An insulation layer is disposed over at least a portion of the conductor, the insulation layer including a window defining the exposed portion of the second electrode. The conductor includes a clip. A conductive tube is electrically coupled to the first electrode; a first insulation layer is disposed over at least a portion of the conductive tube; and a second insulation layer is disposed over at least a portion of the clip. The first insulation layer and the second insulation layer each include Teflon®.

The shaft defines a lumen. The device includes a distal portion and defines a lumen opening at the distal portion, the lumen opening being in communication with the lumen and configured to provide aspiration. A surface area of the exposed portion of the second electrode is at least approximately six times a surface area of the first electrode. The first electrode includes a surface configured to scrape tissue. The first electrode is configured in an ashtray configuration and the surface includes an edge in the ashtray configuration.

The elongated shaft defines a longitudinal axis and includes a distal portion, and the first electrode is coupled to the distal portion of the shaft and is configured to contact tissue straight-on along the longitudinal axis. The elongated shaft includes a distal portion that is malleable to allow a user to bend the shaft. The first electrode is configured to ablate tissue. The entire exposed portion of the second electrode is spaced proximally from the first electrode.

According to another aspect, performing surgery includes applying electrical energy to a first electrode of a bipolar surgical device to perform electrosurgery on a target tissue, the first electrode being disposed on an elongated shaft of the bipolar device. The bipolar device includes a second electrode having an exposed portion disposed around only a part of a circumference of the elongated shaft. Performing surgery also includes providing an insulated surface extending longitudinally along an entire side of the shaft, such that non-target tissue adjacent the insulated surface is shielded during the application of electrical energy to target tissue.

Embodiments of this aspect may include one or more of the following features.

Providing the insulated surface includes providing a thermally and electrically insulated surface. The device includes a bend at a distal portion of the shaft proximal to the first electrode, and providing the insulated surface includes providing a surface extending distally on the shaft only to the bend. Applying electrical energy to perform electrosurgery includes ablating the target tissue. Fluid is aspirated through the shaft. The target tissue is scraped using a surface on the first electrode. The bipolar surgical device is inserted into a body such that the first electrode is adjacent the target tissue. Providing the insulated surface includes using a device that includes a second electrode, the second electrode being coupled to the shaft, electrically isolated from the first electrode, including an exposed portion disposed around only part of a circumference of the elongated shaft, and the exposed portion including a portion that is spaced proximally from the first electrode.

According to another aspect, a surgical device includes an elongated shaft, a first electrode coupled to the shaft, a second electrode coupled to the shaft and including an exposed portion disposed around only part of a circumference of the elongated shaft, and an insulating member coupled to the shaft for providing an insulated surface extending longitudinally along an entire side of the shaft such that non-target tissue adjacent the insulated surface is shielded during the application of electrical energy to target tissue.

Embodiments of this aspect may include one or more of the following features.

The mechanism includes a conductor coupled to the shaft and electrically isolated from the first electrode, the conductor disposed around only part of the circumference of the elongated shaft and including a portion configured to serve as a second electrode. The mechanism for providing the insulated surface includes a mechanism for providing a thermally and electrically insulated surface.

According to another aspect, a surgical device includes an elongated shaft including a first side; a first electrode coupled to the shaft and side-facing toward the first side, and including an exposed portion that is not disposed around an entire circumference of the elongated shaft; and a second electrode coupled to the shaft, electrically isolated from the first electrode, side-facing toward the first side, and including an exposed portion that is not disposed around an entire circumference of the elongated shaft.

Embodiments of this aspect may include the following feature. The side-facing first electrode and the side-facing second electrode face in the same direction on the first side.

These and other features will be better appreciated and understood when considered in conjunction with the following description and the accompanying drawings. It should be understood, however, that the following description, while indicating particular implementations and numerous specific details thereof, is given by way of illustration and not of limitation. Many changes and modifications may be made, and such changes and modifications are within the scope of the claims.

BRIEF DESCRIPTION OF THE DRAWINGS

FIG. 14 is a longitudinal cross-sectional view of a distal portion of a fifth embodiment of an electrosurgical device.

DETAILED DESCRIPTION

Figure 1:
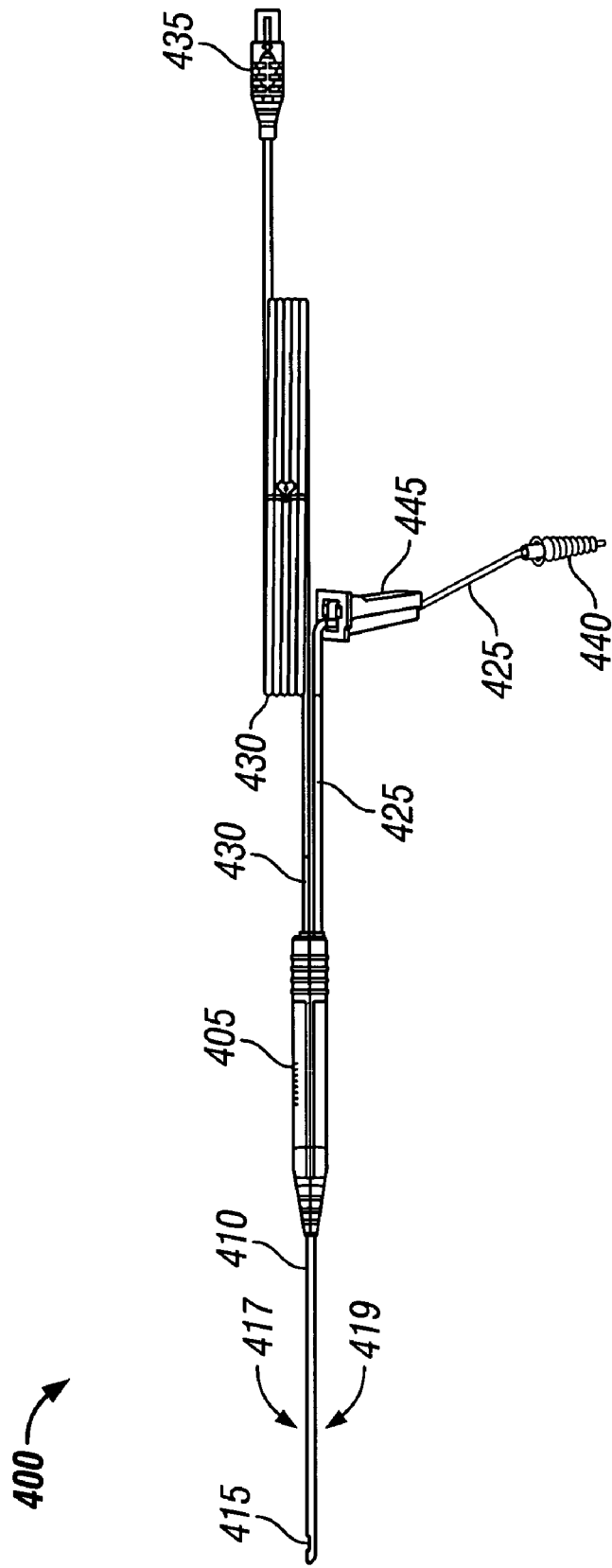
FIG. 1 is a side view of an electrosurgical device.
Figure 2:
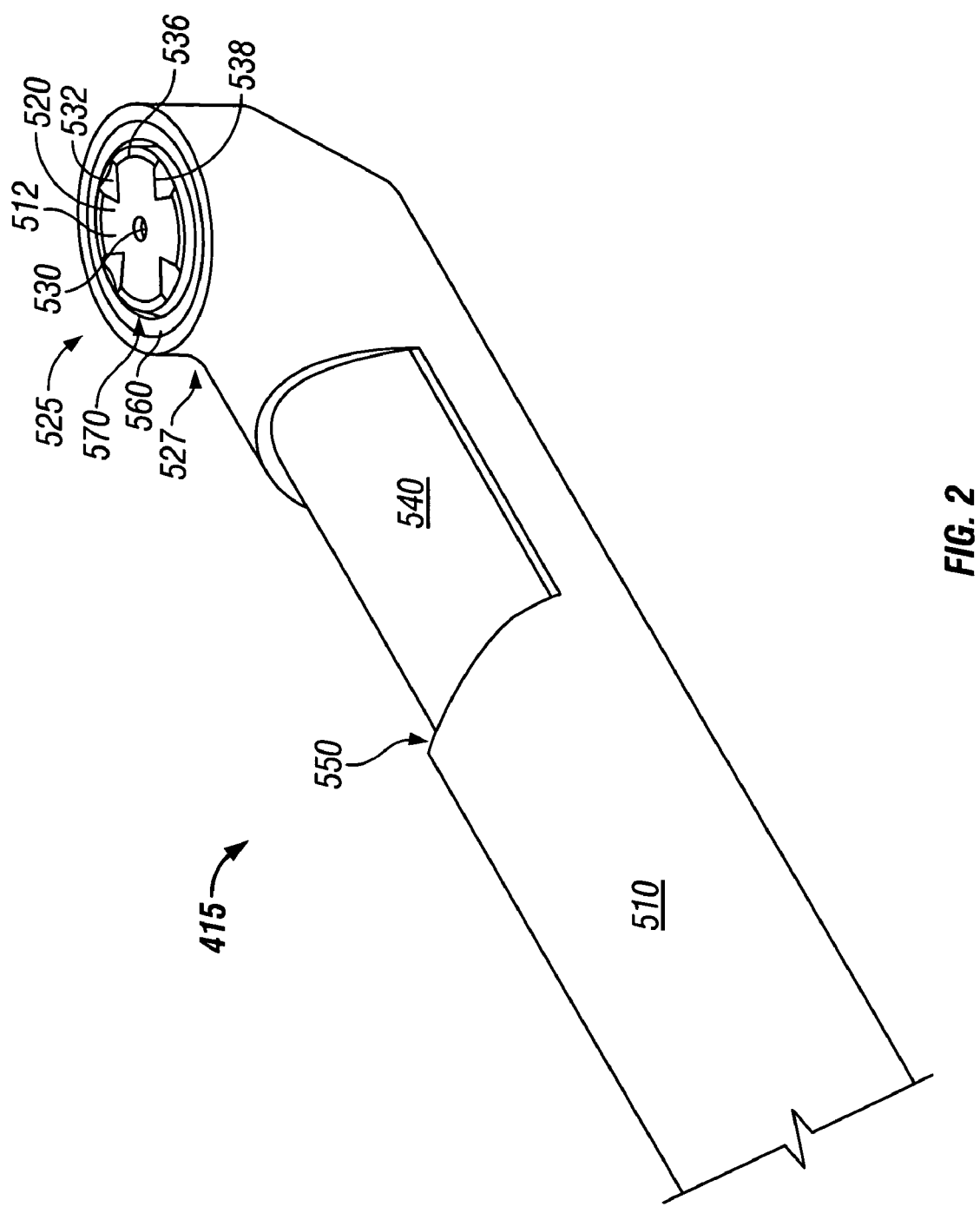
FIG. 2 is a perspective view of a distal portion of the electrosurgical device of FIG. 1.

Referring to FIGS. 1 and 2, a surgical device 400 includes an elongated shaft 410, an active electrode 520 coupled to an end 525 of a distal portion 415 of shaft 410, and a return electrode 540 coupled to distal portion 415 of shaft 410 proximal of active electrode 520 and electrically isolated from active electrode 520. An exposed portion of return electrode 540 is disposed around only part of the circumference of elongated shaft 410 such that return electrode 540 is on only one side 417 (a top side) of shaft 410. On an opposite side 419 of shaft 410, there is a thermally and electrically insulated surface (a "cool back") that acts to shield tissue during electrosurgical use of the device.

Electrosurgical device 400 includes a handle 405 that attaches to a suction tubing 425 and a power cable 430. Power cable 430 carries both active and return power wires to and from an electrosurgical generator (not shown). Power cable 430 has a power connector 435 for attaching cable 430 to a cooperating structure on the electrosurgical generator. Suction tubing 425 has a suction connector 440 for connecting suction tubing 425 to a cooperating standard suction receptacle with a negative aspiration source within an operating room. The amount of suction applied through tubing 425 is controlled by a roller clamp 445 that is applied above suction connector 440. Suction control also can be accomplished, for example, by a series of open ports on handle 405 or a finger activated switch on handle 405.

The assembled length of handle 405 and shaft 410 can be, for example, between 127 to 381 millimeters ("mm"), with the actual length being selected depending on, for example, the size and location of the surgical site. The length of shaft 410 can be, for example, between 76 to 254 mm.

Distal portion 415 has a ninety degree bend 527 such that end 525 and active electrode 520 are side-facing for access to specific anatomies. Different configurations, such as, for example, side-facing configurations having bends of, for example, sixty degrees, forty-five degrees, or thirty degrees, or a configuration having a straight shaft are possible to provide for access to different anatomies within a body.

Active electrode 520 has a concave surface 512 shaped like a shallow dish with an edge 536. In surface 512 there are a sequence of four cutouts 532 providing electrode 520 with an ashtray configuration. Cutouts 532 are formed at four locations along edge 536 spaced approximately ninety degrees apart, have a width that tapers in a radial direction from a maximum at edge 536 to a minimum at approximately half the radial distance to the center of surface 512. Cutouts 532 define additional edges 538 on each side of each cutout 532, and the surface of cutouts 532 is generally concave. A portion 580 of surface 512 (see FIG. 4) lying radially inward from the minimum width of cutouts 532 can be flat. Edge 536, as well as edges 538, provides for a high focusing of electrical current, that is, a high current density, and cutouts 532 further increase the current density at edge 536. Edge 536, as well as edges 538, also provides a mechanical cutting surface. Cutouts 532 also reduce tissue build-up on electrode 520 during use, which increases the electrosurgical performance of electrode 520.

Active electrode 520 defines an aspiration opening 530 for the removal of fluids and particulate matter from the surgical site near active electrode 520. A non-suction probe also can be constructed by sealing aspiration opening 530 to form a solid active electrode. The decision to use a suction or non-suction probe will depend on the particular surgical site and the procedure to be performed by the physician.

Shaft 410 is largely covered by an outer insulation layer 510 that provides electrical and thermal protection. Return electrode 540 is exposed through a return electrode port 550 in outer insulation layer 510. Return electrode port 550 is cut out of outer insulation layer 510 so that port 550 also is side-facing, in the same direction as end 525 and active electrode 520.

Return electrode 540 is proximally spaced from active electrode 520 along shaft 410. The ratio of the area of the exposed portion of return electrode 540 to the area of active electrode 520 is approximately 8:1 and provides for a higher current density at active electrode 520 than at return electrode 540. The ratio can vary in a range from; for example, 2:1 to 10:1 depending on, for example, the application. Electrode 520 and the exposed portion of return electrode 540 are separated by a distance of about 2.5 mm. In another embodiment, the separation distance can vary in a range from, for example, about 2 mm to 10 mm depending on, for example, the application.

Shaft 410 includes an inner insulation layer 560 that surrounds a periphery 570 of active electrode 520, and extends proximally underneath return electrode 540. Edge 536 of active electrode 520 protrudes past inner insulation layer 560 (see FIG. 3). As a result, two layers of insulation surround distal portion 415 to provide electrical and thermal insulation, as further explained with respect to FIG. 5.

Figure 3:
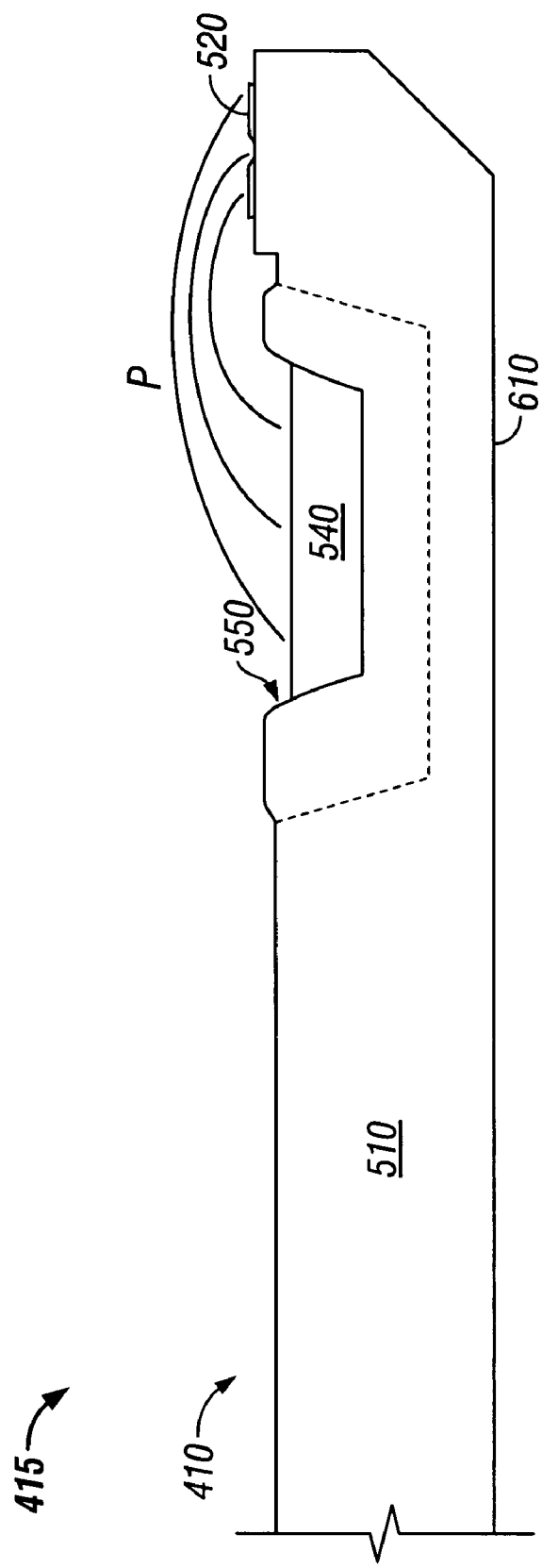
FIG. 3 is a side view of the distal portion shown in FIG. 2.

Referring to FIG. 3, RF energy flowing from active electrode 520 is directed to the exposed portion of return electrode 540 through tissue being treated, and thermal energy generated from a RF current path P is primarily concentrated between active electrode 520 and the exposed portion of return electrode 540 on top side 417 and not on bottom side 419 (see FIG. 1). Because the exposed portion of return electrode 540 only extends along a portion of the circumference of shaft 410, a back (or bottom) portion 610 of shaft 410 and any tissue or structure adjacent back portion 610 are shielded from any direct thermal effects caused by RF current path P between active electrode 520 and return electrode 540. Shielding tissue can include, for example, preventing any tissue effect from occurring in the tissue.

Figure 4:
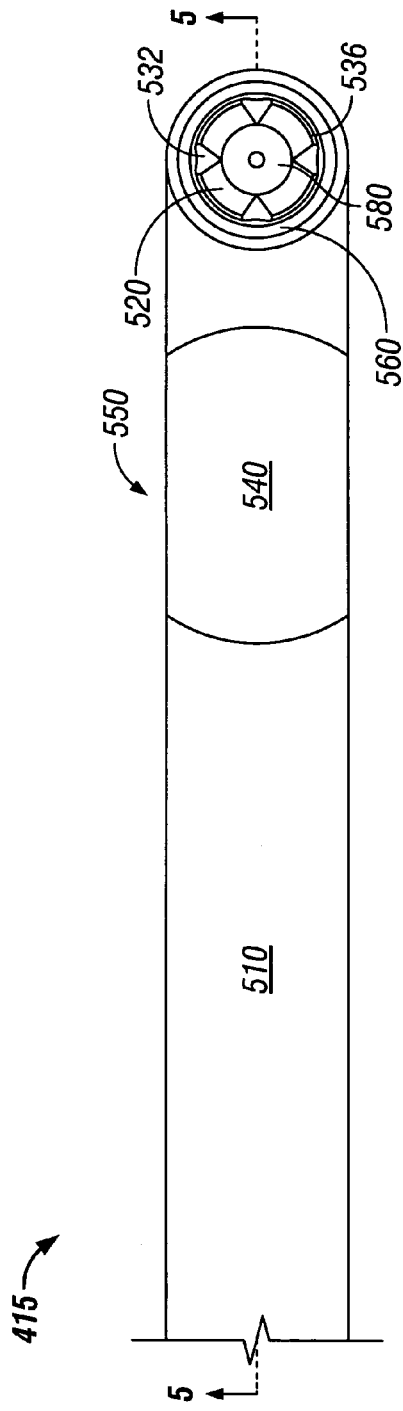
FIG. 4 is a top view of the distal portion shown in FIG. 2.

Referring to FIG. 4, the exposed portion of return electrode 540 and return electrode port 550 are depicted as having an oval shape, although return electrode port 550 can have a variety of shapes, such as, for example, oval or square, depending on the size of the probe and the configuration of active electrode 520.

Figure 5:
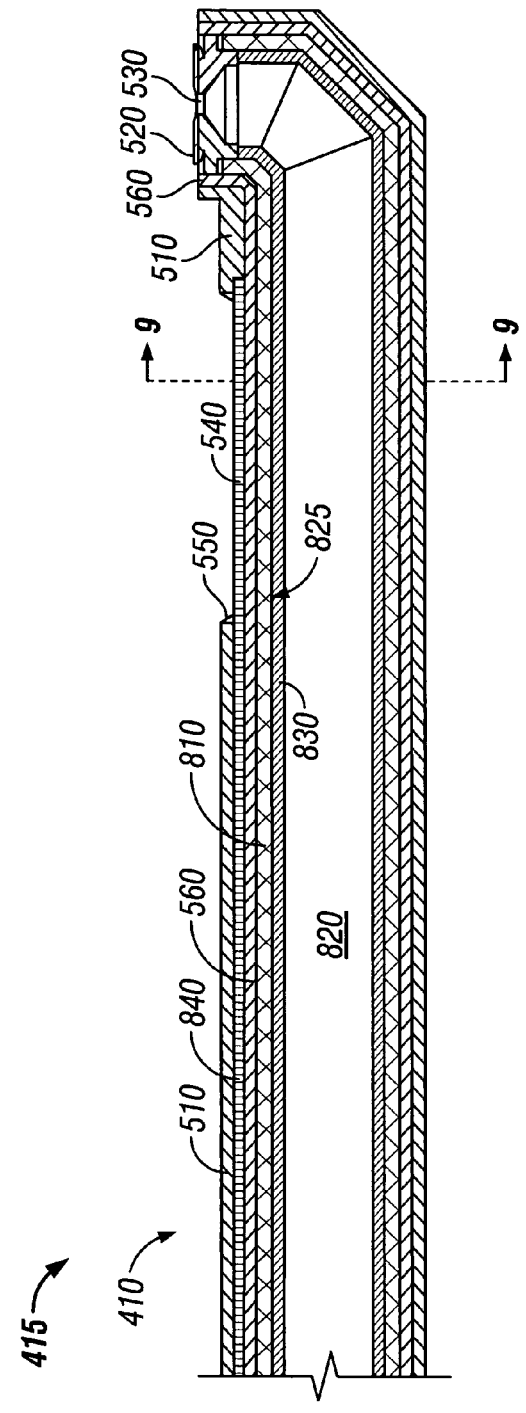
FIG. 5 is a cross-sectional view taken along line 5-5 in FIG. 4.

Referring to FIG. 5, shaft 410 includes an electrically conductive tube 810 that is physically and electrically coupled to active electrode 520. Tube 810 is, for example, a hypotube shaft of stainless steel or another biocompatible and electrically conductive material such as tungsten, nickel, or any alloys, and the coupling between tube 810 and active electrode 520 is, for example, created by a laser weld. Because tube 810 is conductive, power is transmitted to active electrode 520 through tube 810.

Tube 810 defines an internal suction lumen 820 that communicates with aspiration opening 530 and suction tubing 425 (FIG. 1) for aspiration of fluids and tissue. An inner surface 825 of tube 810 is lined by a suction lining 830 that provides thermal insulation so that tube 810 remains cool despite passage of hot fluids and ablated tissue through lumen 820. Lining 830 can be, for example, an insert or a coating such as a polyolefin or plastic lining that can sustain high temperatures. Device 400 provides an integrated design that is sealed from the surgical environment and is sterile and reliable because fluid ingress does not short out points within device 400.

Inner insulation layer 560 covers tube 810 and provides electrical and thermal insulation to tube 810. Located between inner insulation layer 560 and outer insulation layer 510 is a conductor 840 (see also FIG. 6). The exposed portion of conductor 840, defined by port 550, forms the exposed portion of return electrode 540. Inner insulation layer 560 thus provides electrical insulation between tube 810 and conductor 840. Outer insulation layer 510 contacts inner insulation layer 560 along portions of shaft 410 where inner insulation layer 560 is not covered by conductor 840. Inner insulation layer 560 and/or outer insulation layer 510 can be, for example, a shrink tubing material that is electrically and thermally insulating.

Figure 6:
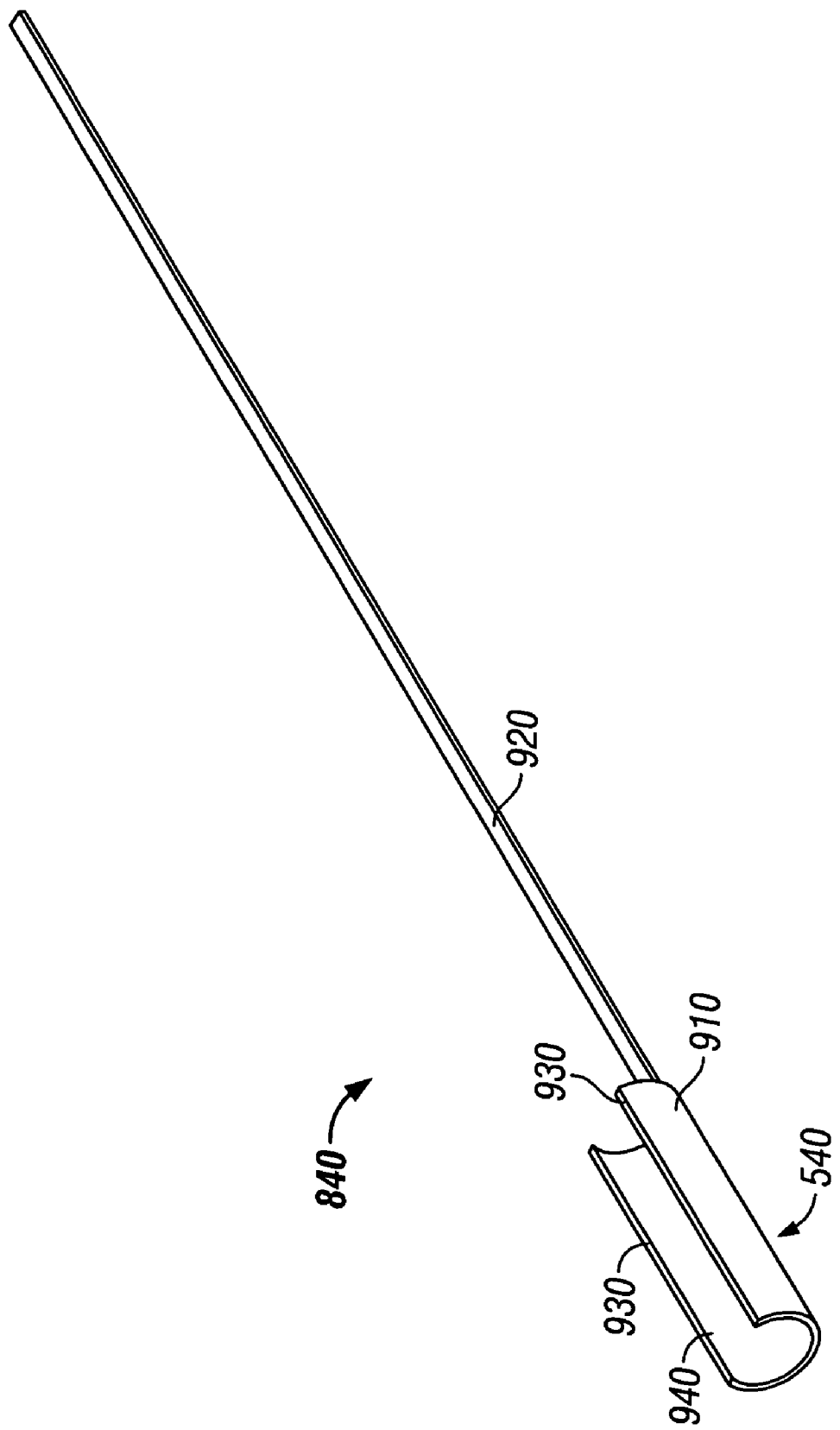
FIG. 6 is a perspective view of a return electrode clip assembly of the electrosurgical device of FIG. 1.

Referring to FIG. 6, conductor 840 includes a conductive clip 910 and a return tab 920. Clip 910 is pre-bent into a cylindrical shape to fit over inner insulation layer 560. Port 550 exposes a portion of clip 910 that defines return electrode 540. Clip 910 can be assembled over inner insulation layer 560 by, for example, sliding clip 910 over inner insulation layer 560. In some implementations, clip 910 is further able to slide between insulation layers 510 and 560 during assembly. Clip 910 also can be assembled, for example, by snapping clip 910 over inner insulation layer 560, with or without the use of a tool to minimize risk of damage of to inner insulation layer 560.

Clip 910 and return tab 920 are formed from a single piece of metal and constitute an integral design, although other implementations need not be integral. In non-integral implementations, clip 910 and tab 920 can be coupled by, for example, crimping, brazing, soldering, welding, or mechanically attaching by using, for example, a spring clip. RF return current flows along tab 920 back to the electrosurgical generator. Return tab 920 is a flat piece of metal, although other implementations can use other structures, such as, for example, a wire. It should be clear that shaft 410 does not include any wires. Further, return tab 920 can be located within an insulated groove located in tube 810 or some other portion of shaft 410. Such a groove can be embedded in shaft 410 such that the cross-sectional profile of shaft 410 remains round.

Clip 910 has edges 930 defining a slot 940 such that clip 910 is not a complete cylinder. Accordingly, when clip 910 is disposed over inner insulation layer 560, clip 910 only extends around a portion of the circumference of shaft 410. In assembly, clip 910 is positioned on shaft 410 such that slot 940 is on bottom side 419 of shaft 410. In operation, because of the narrow width of return tab 920, the return current path does not generally extend into portions of clip 910 that are not between the portion forming the exposed portion of return electrode 540 and tab 920. As a result of the direction of the return current path, back portion 610 (which can have a circumferential extent larger than that of slot 940) is generally free from any thermal energy generated directly from the return current path. Further, because of the limited circumferential extent of clip 910, any thermal conduction within clip 910 away from the return current path does not extend all the way around bottom side 419 of shaft 410.

Accordingly, back portion 610 is substantially non-thermal and protects non-targeted structures and tissue adjacent back portion 610 from thermal damage. As a result, back portion 610 can be rested against thermally sensitive structures while high temperature treatment, such as, for example, cutting or ablation occurs at active electrode 520 on the opposite side of shaft 410. The thermal protection results in a safer application of RF energy.

Figure 7:
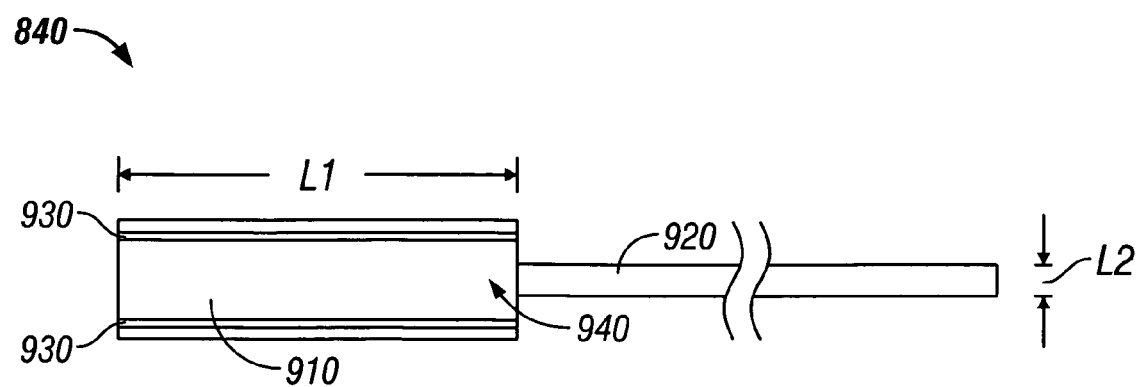
FIG. 7 is a bottom view of the return electrode clip assembly of FIG. 6.

Referring to FIG. 7, clip 910 has a length L1 of, for example, approximately 50 mm, and return tab 920 has a width L2 of, for example, approximately 5 mm. These dimensions are not critical to operation and can vary depending on, for example, the size of the exposed portion of the return electrode and the amount of current. For example, in one application, L1 can vary from about 10 mm to the full length of the shaft, and L2 can vary from about 1 mm to the full circumference of the shaft.

Figure 8:
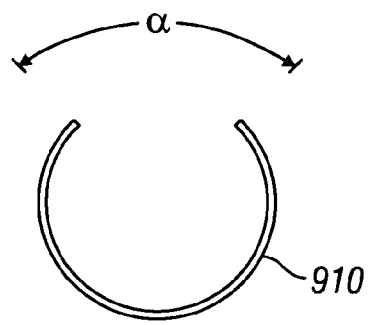
FIG. 8 is a distal end view of the return electrode clip assembly of FIG. 6.

Referring to FIG. 8, clip 910 is about three-fourths of a complete cylinder, that is, slot 940 extends over an arc α of about ninety degrees. These sizes are not critical and can vary depending on, for example, the location of the tissue undergoing surgery. For example, in one application, α can vary from about 0 degrees to 270 degrees.

Figure 9:
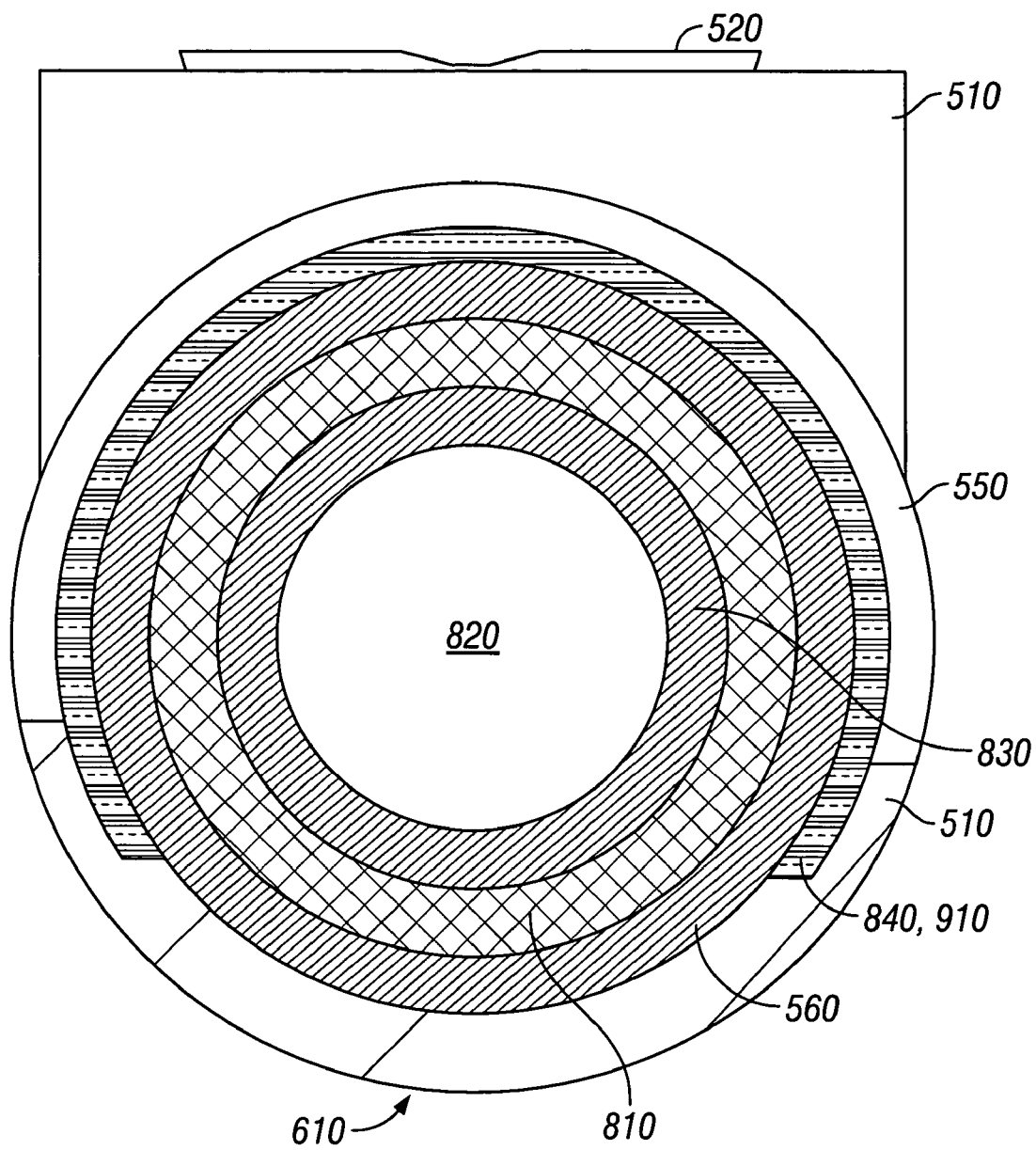
FIG. 9 is a cross-sectional view taken along line 9-9 in FIG. 5.

Referring to FIG. 9, inner insulation layer 560 insulates tube 810 from conductor 840, preventing shorting between tube 810 and conductor 840. A dual layer of insulation is formed from outer insulation layer 510 and inner insulation layer 560 on that part of back portion 610 of device 400 where clip 910 does not encircle outer insulation layer 560. This provides an electrically and thermally insulated "cool back" where minimal electrical and thermal effects occur. As explained earlier, a cool back also can extend to portions of back portion 610 that overlap clip 910 but that do not have any appreciable thermal heating. With such an arrangement, device 400 can be placed and used within a narrow joint space and against thermally sensitive tissue, and such thermally sensitive, non-targeted tissue located opposite active electrode 520 and the exposed portion of return electrode 540 is protected from thermal injury.

The double insulation also has the advantage of protecting against shorting from peeling back which is common with high energy and high heat electrosurgical probes. "Peeling back" refers to a situation in which a part of the insulation at the distal portion peels back and can thereby expose underlying conductive material. With two layers of insulation 560 and 510, shorting does not occur unless both layers 560 and 510 peel back or are otherwise compromised.

Port 550 is defined in outer insulation layer 510 to extend more than 180 degrees about the circumference of layer 510, for example, 210 degrees. Port 550 can extend circumferentially over various angles depending on, for example, the desired surface area of the exposed portion of return electrode 540.

Figure 10:
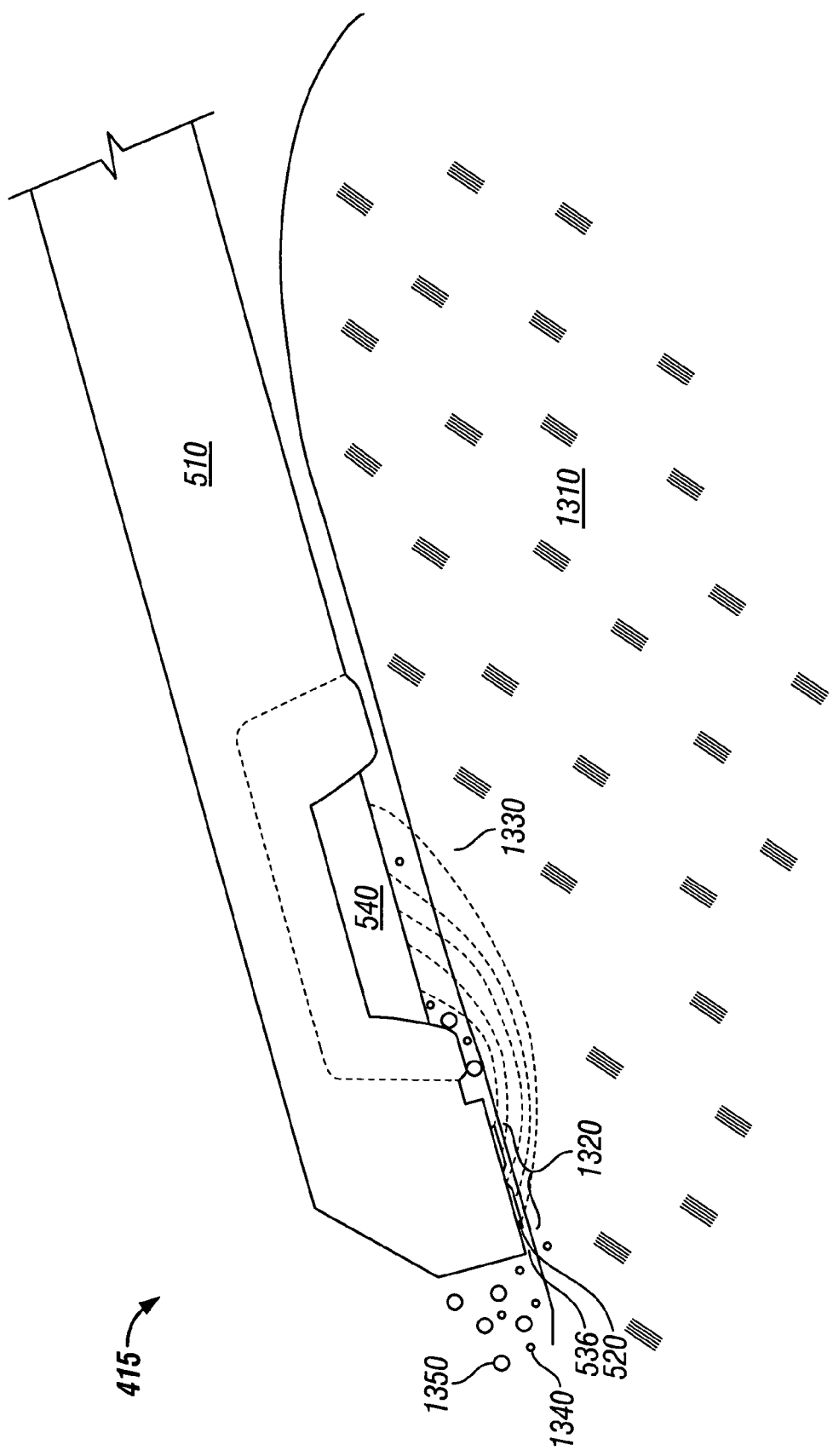
FIG. 10 is a side view illustrating the use of the electrosurgical device of FIG. 1.

Referring to FIG. 10, in use to treat body tissue 1310, edges 536 of active electrode 520 physically contact tissue at a tissue treatment site 1320, providing mechanical and electrical treatment effects. As a surgeon applies power to active electrode 520, RF current flows from active electrode 520 through tissue 1320 along RF current flux lines 1330. If the exposed portion of return electrode 540 is large, then the exposed portion of return electrode 540 can contact tissue, without affecting the tissue.

During application of energy, tissue fragments 1340 and bubbles 1350 created by the high temperatures generated by the RF energy in saline become free floating near device 400. These fragments 1340 and bubbles 1350 can be removed from the surgical site through aspiration opening 530 and suction lumen 820. Alternatively, a separate suction probe can be used.

Active electrode 520 can have different configurations to contact tissue. Edges 536 can be formed for various scraping applications for mechanical tissue treatment or removal, in addition to electrosurgical applications. Active electrode 520 can be molded or pressed to form any shape that can mechanically affect tissue. Examples of electrode configurations include, for example, a clover leaf and a cross fire, as depicted in U.S. Pat. No. 6,461,357. Other insulating structure, such as, for example, an insulating collar can be used to further insulate active electrode 520 from return electrode 540. Return electrode 540 can be formed from a portion of tube 810, using proper insulating regions on tube 810 to electrically isolate the two electrodes 520 and 540.

Figure 11:
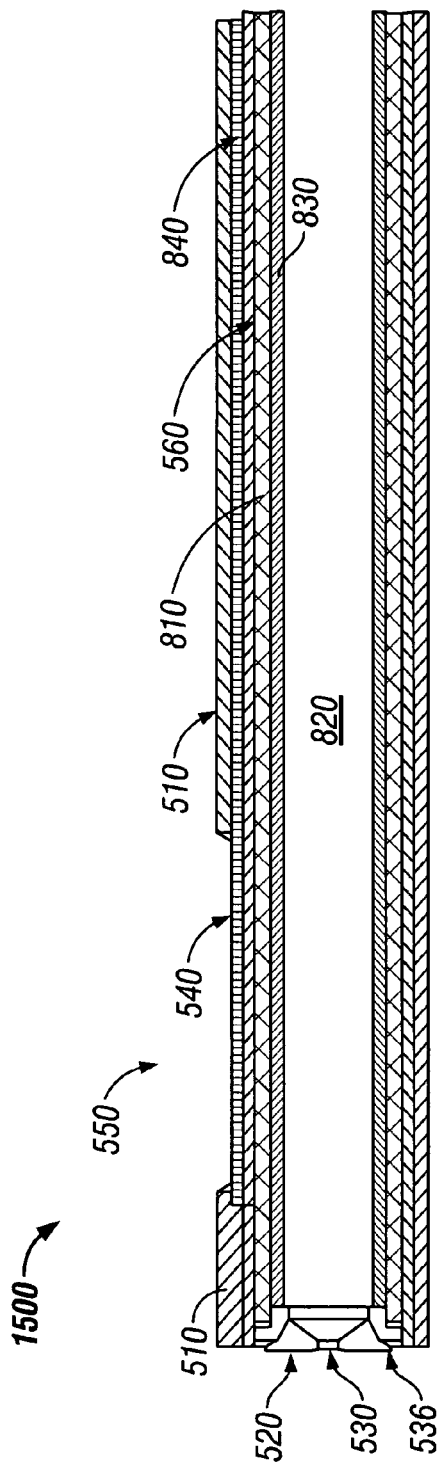
FIG. 11 is a longitudinal cross-sectional view of a distal portion of a second embodiment of an electrosurgical device.

Referring to FIG. 11, rather than being bent at the distal portion, electrosurgical device 1500 has a forward-facing active electrode 520. Device 1500 is otherwise as described above with reference to device 400. Device 1500 can be used, for example, for precise hemostatic cutting and ablation of soft tissue in one convenient device which can be described as a chisel.

Figure 12:
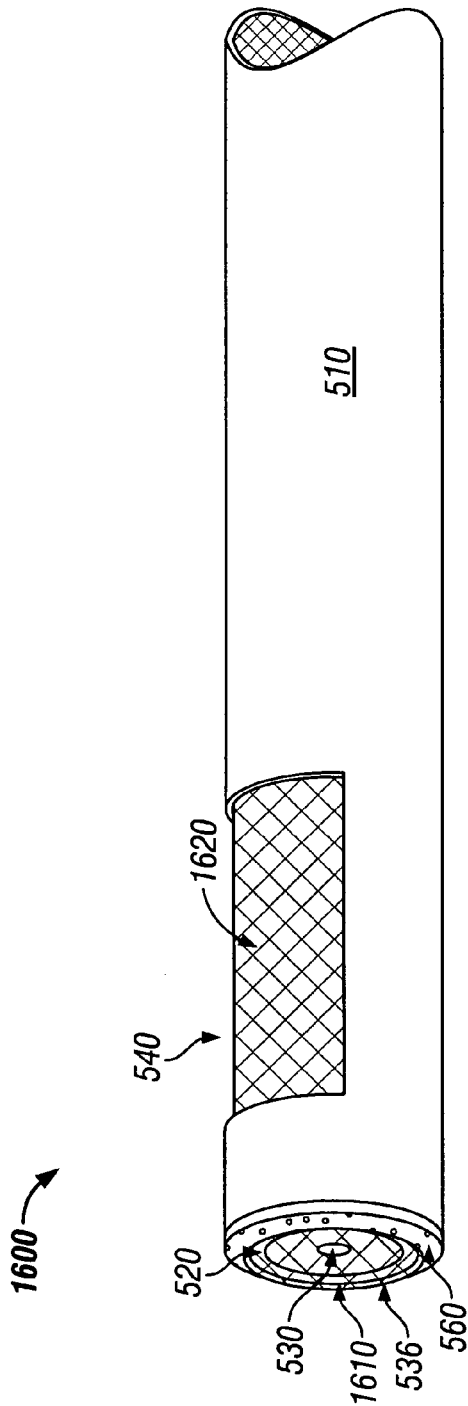
FIG. 12 is a longitudinal cross-sectional view of a distal portion of a third embodiment of an electrosurgical device.

Referring to FIG. 12, an electrosurgical device 1600 shown with a forward-facing active electrode 520 includes an active electrode mesh 1610 covering active electrode 520 and a return electrode mesh 1620 covering the exposed portion of return electrode 540. Meshes 1610 and 1620 are conductive and lie in contact with active electrode 520 and return electrode 540, respectively. Meshes 1610 and 1620 thus form part of active electrode 520 and the exposed portion of return electrode 540, respectively. The use of a mesh provides additional edges (wire conductors) for electrosurgical applications and mechanical scraping, as well as providing additional surface area. Meshes 1610 and 1620 can be disposed over an insulator, in which case meshes 1610 and 1620 constitute the entirety of active electrode 520 and return electrode 540, respectively. Meshes can be used over or in place of the electrodes in the side-facing embodiment of FIG. 1. Meshes, screens, or wire electrodes, for example, having different configurations also can be used depending on, for example, the application and desired electrode characteristics.

The configuration of the probe shaft allows the surgeon to have better access and more selective control while in the operating environment. For example, the electrosurgical probe of FIG. 4 is particularly suitable for use in an arthroscopic acromioplasty wherein the coracoacromial ligament is cut and associated tendons are removed. The right angle of the energy application tip allows the surgeon to scrape target tissue from the underside of the acromion. Various other configurations and geometries of the energy application tip, as shown, for example, in FIGS. 11 and 12, allow the surgeon to perform a variety of arthroscopic procedures to access various joint geometries within the body.

Figure 13:
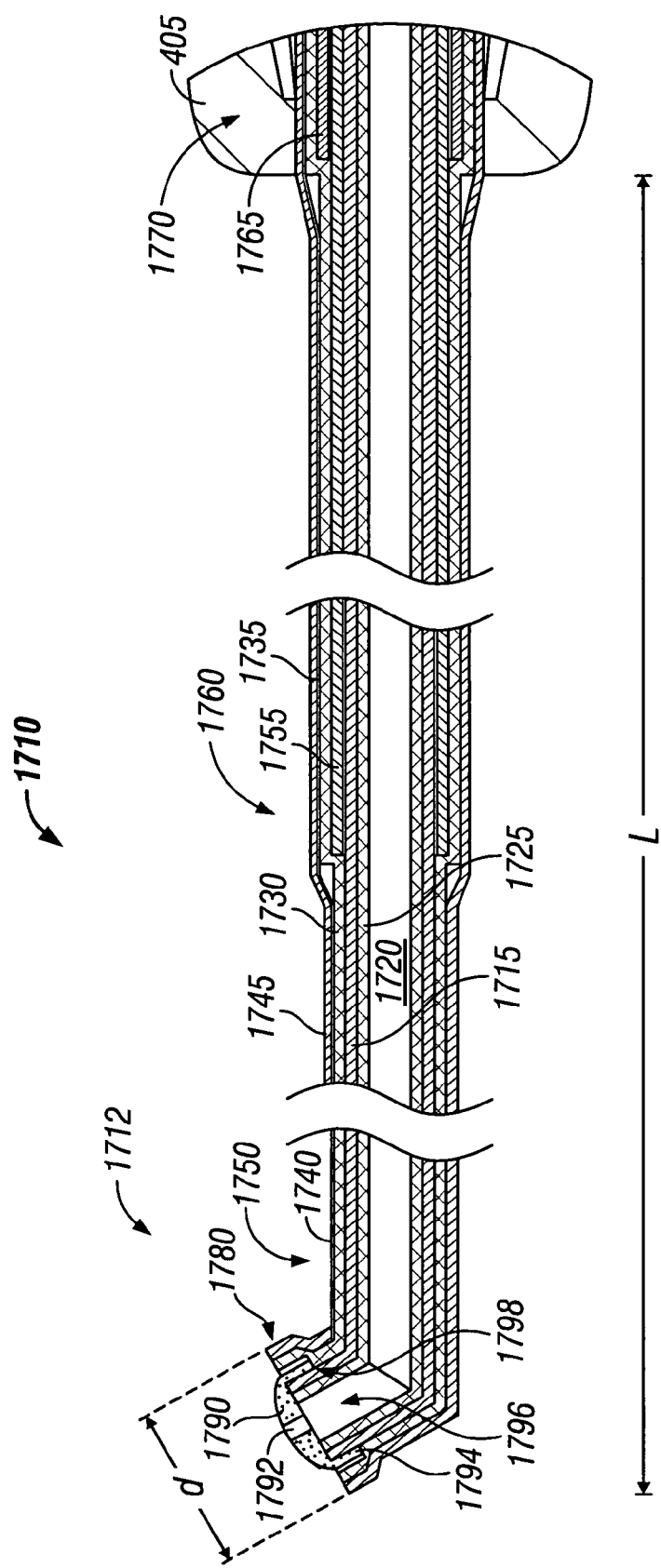
FIG. 13 is a longitudinal cross-sectional view of a distal portion of a fourth embodiment of an electrosurgical device.

Referring to FIG. 13, a shaft 1710 is an alternate implementation of shaft 410. Shaft 1710 has a diameter at a distal portion 1712 that is smaller than the diameter of shaft 410 at distal portion 415. Accordingly, shaft 1710 is advantageously used to perform surgery in small operating environments such as small joint applications, as discussed below. Shaft 1710 mates with handle 405, however, just as shaft 410 does, and so shaft 1710 has a diameter equal to that of shaft 410 at a location 1770 where shaft 1710 mates with handle 405. Shaft 1710 achieves the smaller diameter at distal portion 1712 by stepping down the diameter of shaft 1710 from a maximum at handle 405 to a minimum at distal portion 1712. The step down in diameter is achieved by using three concentric tubes 1765, 1755, and 1715 of decreasing diameter as explained below.

Shaft 1710 includes conductive inner tube 1715 defining a lumen 1720, an inner suction lining 1725, an inner insulation layer 1730, a conductor 1735 that forms a return electrode 1740, and an outer insulation layer 1745 with a cutout 1750 defining an exposed portion of return electrode 1740.

Shaft 1710 also includes conductive middle tube 1755 that is concentric with inner tube 1715. Tubes 1715 and 1755 are crimped together at a location 1760 to secure inner tube 1715 to middle tube 1755. Shaft 1710 further includes conductive outer tube 1765 that is concentric with, and crimped to, both inner tube 1715 and middle tube 1755 at location 1770 to secure outer tube 1765 to both middle tube 1755 and inner tube 1715. Outer tube 1765 has the same diameter as tube 810 of FIG. 5, and handle 405 receives and mates with outer tube 1765 in a manner similar to the manner is in which handle 405 receives and mates with tube 810. Inner tube 1715, middle tube 1755, and outer tube 1765 can each be, for example, a hypotube. Tubes 1755 and 1765 need not be conductive, however. The crimping can be performed, for example, using a four-point crimp.

Attached to a distal end 1780 of shaft 1710 is a dome-shaped active electrode 1790 defining an aspiration opening 1792 in communication with lumen 1720. Electrode 1790 includes a cylindrical side wall 1794 defining a bore 1796 that receives inner tube 1715. Inner tube 1715 is laser welded near a bottom portion 1798 of side wall 1794, and typically on the outside of side wall 1794. Insulation layers 1730 and 1745 are positioned on the outside of side wall 1794. Electrode 1790 receives electrical power from a generator through inner tube 1715 for performing ablation or other electrosurgical procedures.

As explained above, shaft 1710 is advantageously used to perform surgery in small operating environments. Shaft 1710 has a diameter "d" at distal end 1780 of approximately 2 mm and a length "L" of approximately 100 mm. These values can be compared to typical value of approximately 3.5 mm and 150 mm for the implementation shown in FIG. 5. Accordingly, handle 405 is used with devices having electrodes of various sizes and intended to be used in various locations of a body. Shaft 1710 may be preferred by a surgeon for performing electrosurgery on, for example, a wrist, whereas the implementation of FIG. 5 may be preferred by a surgeon for performing electrosurgery on a knee.

Middle tube 1755 typically extends only part of the distance (L) between handle 405 and electrode 1790. The length of this extension affects, for example, the flexibility and rigidity of shaft 1710 and can vary depending on, for example, the application and a surgeon's preference. In particular embodiments, middle tube extends, for example, approximately one-third or two-thirds of the distance L.

Aspiration opening 1792 is electrically conductive and can electrically affect (for example, ablate) tissue lodged within aspiration opening 1792, thus inhibiting clogging of aspiration opening 1792. Further, aspiration opening 1792 has a diameter that is less than the diameter of lumen 1720 to inhibit clogging of lumen 1720. Device 400 of FIG. 1 enjoys the same characteristics.

Referring to FIG. 14, electrosurgical device 1900 includes a dome-shaped active electrode 1910 that does not have an aspiration opening. Active electrode 1910 is coupled to a tube 1915 by a laser weld near a bottom portion 1920 of electrode 1910. Tube 1915 is solid, although a hollow tube can be used as well.

Electrosurgical devices can be malleable or pre-bent to allow for appropriate access and control within the surgical environment. Malleable probe tips, particularly solid probe tips, such as, for example, tube 1915, can be configured by the surgeon or other user as straight, angled, or curved, for example, to provide for optimal access to specific anatomy and pathology. The described tip designs provide tactile feedback from, for example, the edges or other scraping surfaces, and provide for improved tissue visualization by, for example, reducing bubbling and/or charring.

As discussed above, return electrode port 550 is cut out of outer insulation layer 510 so that port 550 also is side-facing, in the same direction as end 525 and active electrode 520. Exposed portions of active and return electrodes can be side-facing in the same direction, as in device 400, or alternatively, the exposed portions of the electrodes can be side-facing in directions that are different. Exposed portions of electrodes that are side-facing in different directions can be circumferentially separated by an angle that is, for example, quite small, such that exposed portions of both electrodes are facing in generally the same direction or at least facing toward the same side of the shaft (for example, the top side 417). Further, for exposed portions of electrodes that, taken as a whole, are facing different directions, there can be portions on each electrode that face the same direction. It should be clear that various configurations in which the exposed portions of the electrodes, taken as a whole, are not facing in the same direction can still provide a cool back.

Materials for the active and return electrodes include, for example, titanium, tungsten, platinum, or nickel based alloys. Other biocompatible metals and alloys generally used in sterile electrosurgical devices also can be used for the electrodes. The shaft of device 400 can be, for example, stainless steel, titanium, platinum, or tungsten and the handle can be made of, for example, Acrylonitrile Butadiene Styrene ("ABS") plastic or other compatible materials.

The various tubes described can have other shapes besides cylindrical, such as, for example, oval and rectangular, and can have a diameter or other size that varies with distal location, such as, for example, that provided in a tapering cylindrical tube. Various other configurations are also possible. For example, an insulative tube can be used as an "inner insulation layer" with an inner conductive coating (or a partial coating, such as, for example, a strip) serving as the mechanism for coupling RF power to an active electrode, and an outer conductive coating (or strip, for example) serving as a return electrode (for example, return electrode 540) and/or a return conductor (for example, return tab 920). Other variations also are contemplated, such as, for example, an insulative tube serving as the "lumen lining" with conductive and insulative coatings, for example, applied to the outer surface of the insulative tube.

Inner insulation layer 560 or outer insulation layer 510 can be, for example, a polytetrafluoroethylene ("PTFE") material and also can include polyamide, plastic, or polyolefin which provide for electrical isolation. Layers 510 and/or 560 can be made from heat shrink tubing including such materials, and heat shrink tubing allows for a quick and easy manufacturing process along with durability and simplified sterilization requirements. In one implementation, device 400 is designed for a single use and is discarded after a single operation.

The power delivered by device 400 is, for example, up to 200 watts. Typical operational power is, for example, 120 watts for ablation and 50 watts for coagulation. For the device of FIG. 13, typical operational power is, for example, 80 watts for ablation and 40 watts for coagulation. The maximum output voltage of the generator powering the devices is, for example, 320 V rms which corresponds to a peak-to-peak voltage of approximately 1000 V. The output frequency of the generator is, for example, 460 kHz sinusoidal, and the output can be unmodulated, that is, have a duty cycle of 100%. RF power can be controlled using, for example, a foot pedal. RF controls also can be provided in handle 405.

To maintain the appropriate temperature for cutting tissue, the distal portion of the probe also can be equipped with a thermal feedback system such as a thermocouple. In one implementation, the thermocouple is connected to two leads and is placed between the active electrode and the exposed portion of the return electrode in order to provide feedback of the actual tip temperature. Other types of temperature feedback circuits can be used. Specific examples include thermistors and thermal integrated circuits. Such temperature feedback circuits return probe temperature information to the generator in order to modulate power, thus changing the energy output and the temperature.

It also will be appreciated that the active electrode can be, for example, brazed, crimped, soldered, welded, or mechanically attached. Further, the active and return electrodes can include, for example, titanium, tungsten, and their alloys, or stainless steel, and the return tab can include, for example, stainless steel in a variety of tensile strengths, titanium, copper, or any suitable alloys thereof.

In particular implementations described, the active electrode generates heat by concentrating RF energy at sharp edges causing, for example, cutting and ablation while the return electrode generates little heat due to the larger ratio of exposed surface area and lack of sharp edges. These distal energy application tips and active electrode designs also can be used in conventional monopolar surgical systems where the return electrode is located on the patient's body.

An example involves a probe being used in the knee joint during a notchplasty procedure for anterior cruciate ligament repair. The probe configuration, in particular the energy application tip configuration, is used to remove and scrape the condylar surfaces of a femur to increase the interchondylar notch to free the anterior cruciate ligament from impingement. The anterior cruciate ligament also can be cut and removed using the probe, and a patellar tendon graft can be performed.

The foregoing description has been presented for purposes of illustration and description. It is not intended to be exhaustive or to limit the claims to the precise forms disclosed. Modifications and variations will be apparent to practitioners skilled in this art. For example, with respect to the disclosed implementations, as well as other implementations, monopolar implementations can be achieved by using a second probe that is independently coupled to the electrosurgical generator, or alternatively, simply by providing an additional electrode as a return electrode on the body of a patient and not activating the return electrode on the probe. These and various other modifications can be made to the disclosed implementations. It is intended that the scope of the invention be defined by the following claims and their equivalents.

What is claimed is:

1. A surgical device comprising:
   an elongated shaft comprising an electrically conductive tube;
   a first electrode coupled to the conductive tube;
   a second electrode coupled to the shaft, electrically isolated from the first electrode, the second electrode including an exposed portion disposed around only part of a circumference of the elongated shaft, and the exposed portion being disposed entirely proximal of the first electrode; and
   an insulator extending longitudinally along an entire side of the shaft such that non-target tissue adjacent the insulator is insulated during electrosurgery.

2. The surgical device of claim 1 further comprising a conductor that includes the second electrode, the conductor being disposed around only a portion of the circumference of the elongated shaft, wherein the insulator is disposed over at least a portion of the conductor and includes a window that exposes the exposed portion of the second electrode.

3. The surgical device of claim 2 wherein the portion of the circumference around which the conductor is disposed is no more than 315°.

4. The surgical device of claim 1 wherein the insulator provides both thermal and electrical insulation.

5. The surgical device of claim 1 wherein the first and second electrodes are each side-facing toward the same side of the shaft.

6. The surgical device of claim 1 wherein the first electrode is forward-facing.

7. The surgical device of claim 1 wherein the first and second electrodes are not disposed on opposite sides of the elongated shaft.

8. The surgical device of claim 1 wherein the device has only two electrodes.

9. The surgical device of claim 1 wherein:
   the first electrode is side-facing, and
   the device can only be configured such that the second electrode is side-facing toward the same side as the first electrode.

10. The surgical device of claim 1 wherein the insulator defines a window that exposes the exposed portion of the second electrode.

11. The surgical device of claim 1 wherein both the first electrode and the second electrode are side-facing away from the insulator.

12. The surgical device of claim 1 wherein the insulator is disposed over at least 45 degrees of a circumference of the elongated shaft.

13. The surgical device of claim 1 wherein the surgical device defines a return path for current that does not go under the insulator.

14. The surgical device of claim 1 wherein:
   the elongated shaft comprises a distal portion, and
   the first electrode is coupled to the distal portion of the elongated shaft and is side-facing.

15. The surgical device of claim 14 wherein:
   the elongated shaft defines a longitudinal axis and comprises a first side extending longitudinally along the axis,
   the side-facing first electrode faces toward the first side, and
   the second electrode includes a portion facing the first side.

16. The surgical device of claim 15 further comprising a conductor that includes the second electrode, the conductor being disposed around only a portion of the circumference of the elongated shaft, and wherein the insulator is disposed over at least a portion of the conductor and the insulator includes a window that exposes the exposed portion of the second electrode.

17. The surgical device of claim 16 wherein the conductor comprises a clip.

18. The surgical device of claim 17 further comprising: a conductive tube that is electrically coupled to the first electrode; and a second insulator disposed over at least a portion of the conductive tube, wherein the conductor is disposed over at least a portion of the second insulator.

19. The surgical device of claim 18 wherein the insulator and the second insulator each comprise Teflon®.

20. The surgical device of claim 14 wherein:
the shaft includes a bend in the distal portion proximal to the first electrode and includes a distal tip, and
the side-facing first electrode is disposed at the distal tip.

21. The surgical device of claim 20 wherein the bend comprises a curve.

22. The surgical device of claim 1 wherein:
the elongated shaft defines a lumen, and
the device comprises a distal portion and defines a lumen opening at the distal portion, the lumen opening being in communication with the lumen and configured to provide aspiration.

23. The surgical device of claim 1 wherein a surface area of the exposed portion of the second electrode is at least approximately six times a surface area of the first electrode.

24. The surgical device of claim 1 wherein the first electrode comprises a surface configured to scrape tissue.

25. The surgical device of claim 21 wherein the first electrode is configured in an ashtray configuration and the surface comprises an edge in the ashtray configuration.

26. The surgical device of claim 1 wherein:
the elongated shaft defines a longitudinal axis and comprises a distal portion, and
the first electrode is coupled to the distal portion of the shaft and is configured to contact tissue straight-on along the longitudinal axis.

27. The surgical device of claim 1 wherein the elongated shaft comprises a distal portion that is malleable to allow a user to bend the shaft.

28. The surgical device of claim 1 wherein:
the first electrode is configured to provide radio frequency energy to ablate tissue, and
the second electrode is configured to operate in a bipolar mode with the first electrode.

29. The surgical device of claim 1 wherein all exposed portions of the second electrode are spaced proximally from the first electrode.

30. The surgical device of claim 1 wherein:
the elongated shaft comprises a proximal portion and a distal portion, the distal portion including a bend;
the first electrode is coupled to the elongated shaft distally of the bend, and
the exposed portion of the second electrode is disposed proximally from the bend.

31. The surgical device of claim 30 wherein the bend comprises a curve.

32. The surgical device of claim 30 wherein:
the proximal portion defines a first longitudinal axis, and
the distal portion defines a second longitudinal axis different from the first longitudinal axis.

33. A surgical device comprising:
an elongated shaft comprising an electrically conductive tube;
a first electrode coupled to the conductive tube;
a second electrode coupled to the elongated shaft and including an exposed portion disposed around only part of a circumference of the elongated shaft, the exposed portion being disposed entirely proximal of the first electrode; and
means coupled to the elongated shaft for providing an insulating surface extending longitudinally along an entire side of the elongated shaft, such that non-target tissue adjacent the insulating surface is shielded during the application of electrical energy to target tissue.

34. The surgical device of claim 33 further comprising a conductor coupled to the elongated shaft and electrically isolated from the first electrode, the conductor disposed around only part of the circumference of the elongated shaft and including a portion configured to serve as a second electrode.

35. The surgical device of claim 33 wherein the means for providing the insulating surface comprises means for providing a thermally and electrically insulating surface.

36. A surgical device comprising:
an elongated shaft including a first side, the elongated shaft comprising an electrically conductive tube;
a first electrode coupled to the conductive tube, side-facing toward the first side, and not disposed around an entire circumference of the elongated shaft;
a second electrode coupled to the elongated shaft, electrically isolated from the first electrode, side-facing toward the first side, and including an exposed portion not disposed around an entire circumference of the elongated shaft, the exposed portion being disposed entirely proximal of the first electrode; and
an insulator extending longitudinally along an entire side of the elongated shaft such that non-target tissue adjacent the insulator is insulated during electrosurgery.

37. The surgical device of claim 36 wherein the side-facing first electrode and the side-facing second electrode face in the same direction on the first side.

38. The surgical device of claim 36 wherein the first and second electrodes are stationary.

39. The surgical device of claim 36 wherein the exposed portion of the second electrode is disposed around only part of the circumference of the elongated shaft.

40. A surgical device comprising:
a shaft comprising an electrically conductive tube;
a first electrode coupled to the conductive tube, the first electrode configured for treating tissue; and
a second electrode coupled to the shaft and configured to operate in a bipolar configuration with the first electrode, the second electrode including an exposed portion disposed entirely proximal of the first electrode, and the exposed portion being disposed around only part of a circumference of the shaft with the remainder of the circumference of the shaft being formed of an insulator such that non-target tissue adjacent the insulator is insulated during electrosurgery.

41. The surgical device of claim 40 wherein the exposed portion of the second electrode is disposed on a first side of the shaft.

42. The surgical device of claim 40 wherein the insulator is disposed along an entire back side of the shaft.

43. The surgical device of claim 40 wherein the insulator is disposed on a first side of the shaft, and the exposed portion of the second electrode is disposed on a second side that is opposite the first side.

44. A surgical device comprising:
an elongated shaft comprising an electrically conductive tube;

a first electrode coupled to the conductive tubes;

a second electrode coupled to the shaft, electrically isolated from the first electrode; and an insulator defining a window that exposes a portion of the second electrode, and the insulator extending longitudinally along an entire side of the shaft such that non-target tissue adjacent the insulator is insulated during electrosurgery.

45. The surgical device of claim 44 wherein the portion of the second electrode is disposed around only part of a circumference of the elongated shaft.

46. The surgical device of claim 41 wherein the portion of the second electrode is disposed entirely proximal of the first electrode.

47. A surgical device comprising:

an elongated shaft comprising an electrically conductive tube;

a first electrode coupled to the conductive tube and including a surface configured to scrape tissue;

a second electrode coupled to the shaft, electrically isolated from the first electrode, the second electrode including an exposed portion disposed around only part of a circumference of the elongated shaft; and an insulator extending longitudinally along an entire side of the shaft such that non-target tissue adjacent the insulator is insulated during electrosurgery.

48. A surgical device comprising:

an elongated shaft defining a lumen configured for fluid transfer, the elongated shaft comprising an electrically conductive tube:

a first electrode coupled to the conductive tube;

a second electrode coupled to the shaft, electrically isolated from the first electrode, the second electrode including an exposed portion disposed around only part of a circumference of the elongated shaft; and an insulator extending longitudinally along an entire side of the shaft such that non-target tissue adjacent the insulator is insulated during electrosurgery.

49. The surgical device of claim 48 wherein the first electrode defines, at least in part, a lumen opening in fluid communication with the lumen.

\* \* \* \* \*

UNITED STATES PATENT AND TRADEMARK OFFICE
CERTIFICATE OF CORRECTION

| | | |
|---|---|---|
| PATENT NO. | : 7,481,807 B2 | Page 1 of 1 |
| APPLICATION NO. | : 10/490979 | |
| DATED | : January 27, 2009 | |
| INVENTOR(S) | : Katherine A. Knudsen | |

It is certified that error appears in the above-identified patent and that said Letters Patent is hereby corrected as shown below:

On Title page 3, item [56], under "Other Publications," delete "MiniTAC™ and MicroTAC-S™—ElectroThermal Arthroscopy Probes, Tissue Temperature Control in Areas of Restricted Access—Micro Ligament Chisel™ Probes," Oratec.RTM., Oratec Interventions, Inc., 1999, 2 pages.". (Second occurrence)

On Title page 4, item [56], under reference "Ligament Chisel...", replace "1998" with --1999--.

On Title page 4, item [56], under reference "Vulcan® EAS®...", replace "fromf" with --from--.

At Col. 5, line 33, replace "from;" with --from,--.

At Col. 13, line 6, (Claim 18), after "comprising:", begin the paragraph that follows with --a--.

At Col. 13, line 8, (Claim 18), begin a new paragraph after the word "and".

At Col. 13, line 30, (Claim 25), replace "21" with --24--.

At Col. 15, line 1, (Claim 44), replace "tubes" with --tube--.

At Col. 15, line 12, (Claim 46), replace "41" with --45--.

At Col. 16, line 9, (Claim 48), replace "tube:" with --tube;--.

Signed and Sealed this
First Day of May, 2012

David J. Kappos
*Director of the United States Patent and Trademark Office*